(12) United States Patent
Westphal et al.

(10) Patent No.: US 11,931,075 B2
(45) Date of Patent: *Mar. 19, 2024

(54) FERTILITY KITS WITH STERILE SYRINGES AND COLLECTION JARS, METHOD OF STERILIZATION AND USE

(71) Applicant: PherDal, Dixon, IL (US)

(72) Inventors: Jennifer Westphal, Dixon, IL (US); Ryan Westphal, Dixon, IL (US)

(73) Assignee: PherDal, LLC, Dixon, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/048,425

(22) Filed: Oct. 20, 2022

(65) Prior Publication Data

US 2023/0149044 A1 May 18, 2023

Related U.S. Application Data

(63) Continuation-in-part of application No. 17/526,705, filed on Nov. 15, 2021, now Pat. No. 11,529,172.

(51) Int. Cl.
*A61B 17/43* (2006.01)
*A61B 10/00* (2006.01)
(Continued)

(52) U.S. Cl.
CPC .......... *A61B 17/43* (2013.01); *A61B 10/0058* (2013.01); *A61D 19/027* (2013.01);
(Continued)

(58) Field of Classification Search
CPC .... A61B 17/43; A61B 10/0058; A61D 19/02; A61D 19/027; A61M 5/3134; A61M 5/3137; A61M 5/31513
See application file for complete search history.

(56) References Cited

U.S. PATENT DOCUMENTS 1,589,046 A 6/1926 Harold
3,672,369 A 6/1972 Brown
(Continued)

FOREIGN PATENT DOCUMENTS

CN 200514827 U 8/2016
EP 0538321 * 3/1993 ............ A61M 5/315
(Continued)

OTHER PUBLICATIONS

Mosie Baby Kit website, "Artificial Insemination at Home with Mosie", downloaded Apr. 19, 2022.
(Continued)

*Primary Examiner* — Carrie R Dorna

(57) ABSTRACT

A sterile Intracervical Insemination (ICI) fertility kit, method of sterilization, and method of use for performing self-insemination. Each sterile kit comprises: up to three sets of individually wrapped sterile, disposable, syringes and semen collection jars; printed instructions; and a QR code. The collection jar comprises a snap-on lid, and an inner surface with seamless edges to prevent semen residue. The syringes and jars are sealed in plastic wraps permeable to air and gas, and impermeable to pathogens; and are sterilized via gamma radiation or ethylene oxide. Fresh or frozen, unwashed or washed, semen is deposited into the jar, pulled into the syringe, and administered cervically during a user's maximum monthly level of luteinizing hormone. The syringe distal end is designed to push all semen out of the syringe then plug the end closed, while preventing semen residue from collecting within the syringe. Large circular syringe handles facilitate stable handling.

24 Claims, 9 Drawing Sheets

(51) Int. Cl.
  *A61D 19/02* (2006.01)
  *A61L 2/08* (2006.01)
  *A61L 2/20* (2006.01)
  *A61M 5/315* (2006.01)
  *A61M 5/31* (2006.01)

(52) U.S. Cl.
  CPC .............. *A61L 2/081* (2013.01); *A61L 2/206* (2013.01); *A61B 10/0012* (2013.01); *A61L 2202/122* (2013.01); *A61L 2202/181* (2013.01); *A61L 2202/24* (2013.01); *A61M 5/3134* (2013.01); *A61M 5/31513* (2013.01)

(56) References Cited

U.S. PATENT DOCUMENTS

| | | | |
|---|---|---|---|
| 4,925,449 | A | 5/1990 | Saez et al. |
| 7,022,112 | B2 | 4/2006 | Pokorney |
| 8,114,345 | B2 | 2/2012 | Dlugos, Jr. et al. |
| 10,231,755 | B2 | 3/2019 | Brown et al. |
| 10,773,014 | B2 | 9/2020 | Dickinson |
| 10,864,067 | B2 | 12/2020 | Jun |
| 11,350,967 | B2 | 7/2022 | Brown et al. |
| 11,529,172 | B1 | 12/2022 | Westphal |
| 2002/0193658 | A1* | 12/2002 | Simmet ............... A61D 19/04 600/33 |
| 2011/0224482 | A1 | 9/2011 | McCarthy |
| 2014/0013718 | A1 | 1/2014 | Maasarani |
| 2014/0309488 | A1* | 10/2014 | Fowler ............... A61B 17/43 600/35 |
| 2017/0368226 | A1* | 12/2017 | Pilkington ........ A61M 5/31513 |
| 2018/0140409 | A1 | 5/2018 | Jun |
| 2021/0386456 | A1 | 12/2021 | Plessala et al. |

FOREIGN PATENT DOCUMENTS

| | | | | |
|---|---|---|---|---|
| EP | 1358856 | * | 5/2003 | ............. A61D 19/02 |
| EP | 3744308 | A1 | 12/2020 | |
| WO | WO 2020/077122 | * | 4/2020 | ............. A61B 17/43 |
| WO | WO2023086683 | A2 | 5/2023 | |
| WO | WO2023086683 | A3 | 9/2023 | |

OTHER PUBLICATIONS

Mosie Baby Ovulation Kit website downloaded Feb. 6, 2023.
List of references in U.S. Appl. No. 17/526,705.
Office action mailed U.S. Appl. No. 17/526,705 dated Jan. 20, 2022.
Response for U.S. Appl. No. 17/526,705, filed Apr. 19, 2022.
Office action mailed U.S. Appl. No. 17/526,705 dated May 25, 2022.
Request for Continued Examination response for U.S. Appl. No. 17/526,705, filed Aug. 25, 2022.
Notice of Allowance for U.S. Appl. No. 17/526,705 dated Oct. 4, 2022.
"Transfer of Sterilization Dose, Verification Dose and Maximum Acceptable Dose Between Radiation Sources", Steris, printed Feb. 2019, pp. 1-3.
BSI Standards Publication, Sterilization of Healthcare Products—Ethylene Oxide, Jul. 2014, pp. 1-94.
Sterilization of Medical Devices, FDA, downloaded Feb. 5, 2023.
Dr. Stephen, Reisbacher, "Introduction to Ethylene Oxide Sterilization and Regulatory Updates", Sterigenics and Nelson Labs, May 22, 2019, p. 1-54.
"Gamma Sterilization of Medical Devices", FDA Medical Device Advisory Meeting, Nov. 6, 2019, pp. 1-15.
ISO 11607-1:2019, "Packaging for terminally sterilized medical devices—Part 1: Requirements for materials, sterile barrier systems and packaging systems", downloaded Feb. 5, 2023. Abstract.
ISO 11135, "Sterilization of Health-care products—Ethylene Oxide. Requirements for the development, validation, and routine control of sterilization process for medical devices", Jul. 15, 2014.
ISO-11137-1, "Sterilization of Healthcare Products—Radiation", Apr. 15, 2006.
ISO 11135, "Sterilization of Health-care products—Ethylene Oxide. Requirements for the development, validation, and routine control of sterilization process for medical devices, Amendment, Annex E, Single Batch Release", Oct. 2018.
Pub 1581, IAEA Radiation Technology Series 4, 2013.
Gillet, Annick, "Sterilisation of your Medical Device", Sterigenics, Mar. 5, 2020.
International search report for PCT/US2022/053316 dated Aug. 8, 2023.

* cited by examiner

FERTILITY KITS WITH STERILE SYRINGES AND COLLECTION JARS, METHOD OF STERILIZATION AND USE

CROSS REFERENCE TO RELATED APPLICATION

The present application claims priority as a continuation-in-part to U.S. patent application Ser. No. 17/526,705, now allowed, that was filed on Nov. 15, 2021; and in which the disclosure is incorporated by reference herein in its entirety.

FIELD OF THE INVENTION

The present invention relates generally to sets comprising fertility syringes and semen collection jars for use in at-home intracervical insemination (ICI), applicator kits, and methods of use.

BACKGROUND OF THE INVENTION

Intrauterine Insemination (IUI) requires delivery of washed semen via a syringe through the cervix and directly into the uterus; while Intracervical Insemination (ICI) requires delivery of unwashed semen only to the cervical opening. Methods and instruments for conducting IUI and ICI fertility treatments are well known in the art. IUI requires treatments within a clinical setting, to include taking oral and/or injectable fertility drugs, and the washing of semen. Treatment costs on average about $895; but it can run up to $4000 depending on the clinic (Gurevich, R. *What is Intrauterine Insemination*, published Nov. 11, 2020 on website VeryWellFamily).

A 2018 study showed that during non-medically induced ovulation, Intrauterine Insemination (IUI) and Intracervical Insemination (ICI) have the same live birth rate (Kop, P. A., Mochtar, M. H., et al. (2018). "Intrauterine insemination versus intracervical insemination in donor semen treatment" *The Cochrane database of systematic reviews*, 1 (1)).

ICI is a much less expensive treatment (e.g., the cost of the kit shipped to a user's home). The additional preparation of washing semen, along with needing to be inside of a clinical setting, results in IUI being approximately 4 times the cost of ICI. Due to the high difference in cost, as well as the insignificant difference in live birth rate, it's been suggested that over the initial three months, ICI should be the preferred initial treatment (Kop, PAL, et al. (2015) "Intrauterine insemination or intracervical insemination with cryopreserved donor semen in the natural cycle: a cohort study", *Human Reproduction*, 30 (3)).

Fertility syringes for both IUI and ICI methods are well known in the art; but most available syringes are generally intended for use within a medical setting by a clinician for IUI treatments. IUI syringes are generally thinner and longer than ICI syringes in order to extend through the cervix for direct delivery of semen into the uterus. ICI syringes are generally round at the distal end to block the cervical opening to prevent the released semen from traveling backward into the vagina. ICI syringes can be difficult to handle by users who are not medical professionals, e.g. pushing the plunger in with one hand while lying down.

ICI kits occasionally include a semen collection jar in addition to the fertility syringe. Unfortunately, the jars normally comprise traditional round containers with inside seams or cracks where semen can become trapped, thus reducing the amount that can be transferred to the syringe.

Current sterilized syringes are often not designed for insemination, while at home insemination syringes are not sterilized. Research on the vaginal microbiome and diagnoses of infertility have becoming increasingly present in the art. This research demonstrates the need for sterilized at home syringes, designed for intracervical insemination within the art to reduce likelihood of introducing infection. (Xu et al., (2020) "Fertility factors affect the vaginal microbiome in women of reproductive age" *American J of Reproductive Immunology*, 83 (4); Garcia-Velasco, J, et al. (2020) "The reproductive microbiome—clinical practice recommendations for fertility specialists", RBMO, 41 (3): 443-453; Garcia-Velasco, J, et al. (2017) "What fertility specialists should know about the vaginal microbiome: a review", *RBM online*, page 103-112; and Gupta, S, et al. (2019) "Crosstalk between Vaginal Microbiome and Female Health: A review", *Microbial Pathogenesis*, 136 (103696): 1-10).

What is needed in the art of at-home ICI treatments, is sterilized disposable fertility syringes and semen collection jars for use by non-medical professionals to significantly reduce the costs of treatment while increasing the efficacy in delivering the maximum amount of semen to the user's cervix. At a minimum, the fertility syringes should be easy to use with one-hand; the collection jars should be seamless inside; and the syringe structure should be able to deliver all of the semen to the target site while leaving a minimum amount in the syringe. Additionally, the kits comprising the syringes and the jars should be sterilized to prevent pathogens from hindering the user's fertility.

SUMMARY OF THE INVENTION

Various embodiments of the present invention comprise a fertility kit for performing self-insemination, comprising a container storing one to three sets of the disposable sterilized ICI fertility syringes and a semen collection jar, each wrapped in a pathogen proof plastic and having undergone sterilization. The present invention also includes methods of sterilization and methods of kit use.

Each fertility syringe comprises: an outer rigid tubular barrel and an inner plunger. The barrel comprises a curved distal end with a small circular distal opening, and a sealed proximal end, and an inner hollow tube housing the plunger. The barrel's proximal end also comprises two opposing circular members to fit a user's fingers; and a plunger flat end fitting in-between. The plunger distal end has a circular rubber with a tubular member that fits into the barrel curved end to push all the semen out while preventing a backflow. The collection jar comprises a sealable lid, and an inner surface comprising smooth seamless edges. Fresh or frozen, washed or unwashed semen is deposited into the jar, pulled into the syringe, and administered intra-cervically during a user's maximum monthly level of luteinizing hormone.

Various embodiments of the present invention further comprise an intracervical insemination (ICI) fertility kit for performing at home self-insemination, comprising at least one set (e.g. preferably three sets) of disposable: a) a plastic sterile fertility syringe; and b) a plastic sterile semen collection jar, individual wrapped sterile packing, which are shipped together in a package with instructions.

The sterile ICI fertility syringe comprises: a) an outer rigid tubular barrel comprising a curved distal end with a distal opening and a sealed proximal end, and said barrel enclosing an inner hollow tube with a narrowed distal opening joined to the barrel distal opening; b) the barrel sealed proximal end further comprising a handle combination comprising two opposing substantially hollow circular members able to fit a user's fingers; and c) a plunger positioned within the inner hollow tube and able to slide within to draw up and expel semen from the distal opening.

The plunger further comprises a distal end encircled by rubber seal positioned to tightly fit within (or flush to) the barrel curved distal end. And the plunger further comprises a tubular end distal to the rubber seal, said tubular end positioned to fit tightly within the tube narrowed distal opening to push all of the semen out of the distal opening. And the plunger further comprises a proximal end comprising a flat handle positioned to fit within the barrel circular members when the syringe is closed/retracted. And the plunger further comprises parallel ribs, divided into three sections of equal length, encircling and extending the length of the plunger.

The sterile semen collection jar comprises a plastic handheld container and a sealable lid, and an inner surface comprising smooth seamless edges to prevent semen from being trapped within the seamless edges. It holds about 34 milliliter volume; and is round shaped on the outer bottom surface and inner bottom surface. In an embodiment, the semen collection jars comprise a screw top or snap on lid. With a screw top, threads on the lid match threads on the container-jar.

The ICI fertility kit further comprises a transparent or opaque plastic wrapper sealing one or more of the fertility syringes and semen collection jars to keep them sterile. The wrappers comprise pores able to pass air, gamma radiation, and ethylene oxide gas, but that are too small to permit the passage of pathogens (e.g. bacteria and viruses) into the wrapper.

The ICI fertility kit further comprises a container or box or package for shipping the one or more sets, said package comprising a printed instructions on a method of using the fertility kit, and/or a printed website link or QR code to the instructions.

In an embodiment, the ICI fertility kit may further comprise an ovulation calendar to track luteinizing hormone result levels; and/or luteinizing test strips.

Various embodiments of the present invention further comprise a kit enclosing a plurality of individually packaged sterile fertility syringes and semen collections jars, such as three sets thereof. If the kit comprises one set of syringe and collection jar, then a user will need three kits for a one-month treatment. If the kit comprises three sets of syringes and collection jars, then the user will only need one kit for one month of treatment.

In an embodiment, the semen collection jars comprise a screw top or snap on lid; and round edges on the outer surface and inner walls. The later prevents the semen from collecting in the jar's inner seams, thus making the majority of the semen able to be extracted from the jar into the fertility syringe.

The present invention further comprises a method of sterilization of a plurality of ICI syringes and collection jars, comprising:
1) sealing an ICI fertility syringe and a semen collection jar in a plastic wrap, wherein the syringe and the jar are in the same wrap or a different wrap, and the plastic wrap is non-penetrable to pathogens;
2) determining a sterilization dose level and duration, and setting a sterilization machine to the dose level, wherein the sterilization machine is ethylene oxide or gamma radiation;
3) placing a plurality of the wrapped syringes and the jars into sterilization machine, and exposing for at the determined dose level and duration; and
4) removing the plurality of wrapped syringes and jars from the sterilization machine, and placing one to three sets of the syringes and jars into a kit.

In an embodiment, the sterilization machine emits gamma radiation at a dose level up to 10,000 kilograys, preferably 20-50 kGy, and for a duration up to 24 hours. In an embodiment, the gamma radiation is from Cobalt 60. In another embodiment, the sterilization machine emits ethylene oxide up to 7 days duration.

In an embodiment, the sterilization machine emits ethylene oxide, and requires up to seven days processing.

The present invention further comprises a method of use of the kit disclosed herein to complete a one-month round of at-home fertility treatments, comprising the steps of: 1) providing a fertility kit housing one-three sets of sterile fertility syringes and collection jars; 2) determining a user's calendar date of displaying a maximizing luteinizing hormone levels; 3) receiving a fresh or frozen deposit of a semen sample within the collection jar; 4) holding an unwrapped, sterile fertility syringe vertically in the collection jar, and withdrawing all of the semen sample into the fertility syringe by pulling upward on the plunger; 5) while lying down, inserting the sterility syringe until it is flush with a user's cervical opening, then pushing the plunger one or two-handedly inward to release all of the semen sample into the cervix; 6) remaining lying down for at least a half hour; and 7) repeat steps (1)-(6) two times per month with the two remaining sets of syringes and jars. The treatments are done in three consecutive days. The first application is the day before the user has reached their maximum luteinizing hormone level for the month. The second application should be done on the day of the users maximum luteinizing hormone level, and the third application the day after the luteinizing hormone peak.

One aspect of the present invention is to provide a fertility syringe that is able to reach the cervical opening to provide targeted delivery of the semen directly to the cervical opening. This decreases the distance the semen needs to 'swim' to meet the egg. This is especially helpful for anyone experiencing male factor infertility, such as decreased semen motility or abnormal semen morphology.

Another aspect is that the fertility syringes are sterilized, and then packaged in sterile, plastic wraps. Scientific studies have linked certain bacterial species present in the vaginal microbiome to women with unknown (or idiopathic) infertility. The sterilized syringes of the present invention bypass these bacteria if present. Sterilized syringes also decrease the introduction of new bacteria into the microbiome, which can impact fertility.

Another aspect is that the large opening of the syringe tip combined with the scientifically engineered plunger cap, works to minimize semen sample waste so that the maximum amount of semen is dispersed from the syringe leaving a minimal residual semen within the syringe.

Another aspect is a novel syringe with an elongated and curved distal tip, with a circular opening to maximize a user's chances of impregnating by reaching to, and increasing the surface area contact with the user's cervix. The curved end allows insemination to occur directly at the cervical opening.

Another aspect is the structure of the plunger and barrel distal end to create a one-way like valve that prevents the semen from remaining in the syringe when the plunger is completely pushed in. This is due to the plunger's funnel like end and pointed tip, pushing all semen out of the barrel's hollow tube hole, which is aligned with the barrel outer hole. The plunger's pointed tip plugs these holes to prevent any backwash of the semen.

Another aspect is the novel syringe's combination handle that allows the user to hold the syringe one-handedly, while pushing the plunger completely in. The user holds the syringe with their index and middle finger through the barrel circular loops, and pushes the plunger in with their thumb; and while lying on their back, preferably on a pillow or with their hips otherwise elevated.

Another aspect is the collection jars hold unwashed, fresh or frozen semen.

The objects features and effects of the invention are described in detail below with accompanied drawings and embodiments. The aforementioned objects of the present invention are attained by an apparatus and method that functions for fertilization. Other objects, advantages and novel features of the present invention will become readily apparent from the following drawings and detailed description of preferred embodiments.

BRIEF DESCRIPTION OF THE DRAWINGS

The above and other features, aspects, and advantages of the present disclosure will become better understood with regard to the following description, appended claims, and accompanying drawing herein.

DETAILED DESCRIPTION OF EXEMPLARY EMBODIMENTS

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

And although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As used herein, the term "assembly" and "unit" and "apparatus" may be used interchangeably.

As used herein, the term "proximal" refers to the end of the syringe closest to the user's hands and comprising the end where the user pushes the plunger in/out; and the term "distal" refers to the end of the syringe furthest from the user's hands, and where the semen is ejected from.

As used herein, the term "substantially" and "generally" refers to being significantly similar to the indicated shape or amount as recognized by one of ordinary skill in the art.

As used herein, the term "about" refers to plus or minus 10% of the recited value, e.g.; within +/−5%; within +/−2%; etc.

Figure 3A:
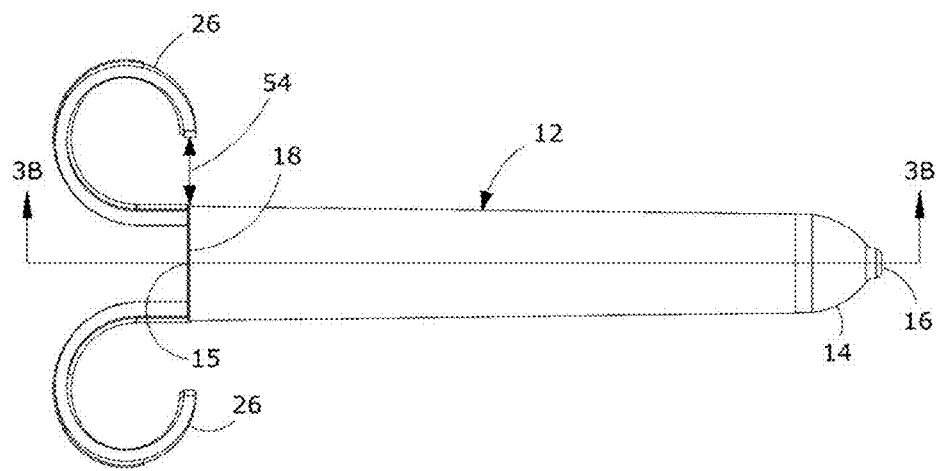
FIG. 3A is a side view of the outer surface of the barrel showing the curved handles for the index and middle finger.
Figure 3B:
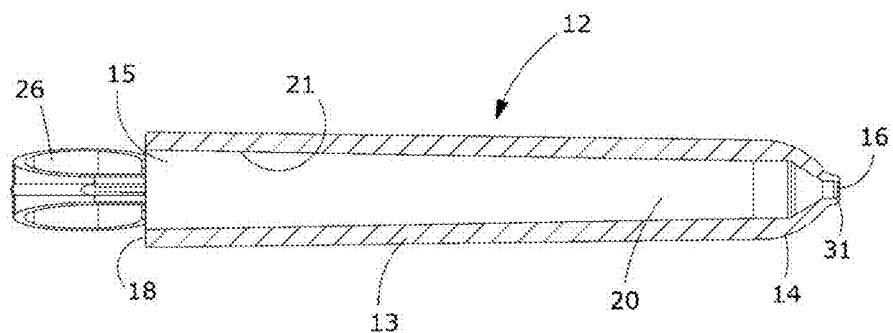
FIG. 3B is a cross-sectional view of an embodiment of the syringe showing the barrel is solid except for the inner hollow tube, which has a funnel-like distal end matching the plunger's distal end.
Figure 4A:
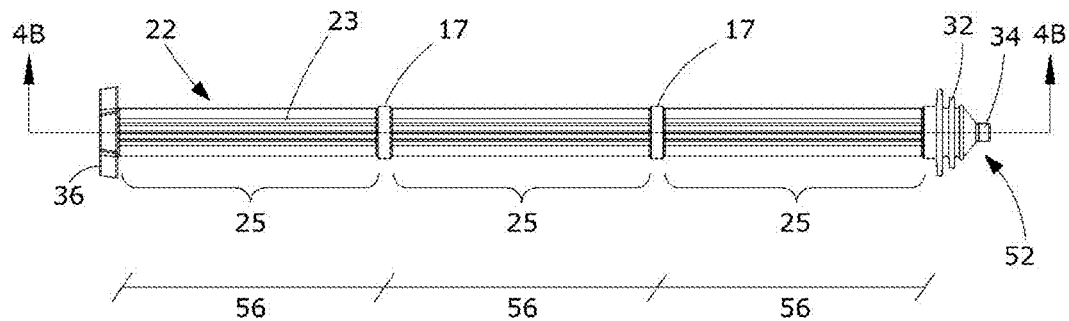
FIG. 4A is a side view of an embodiment of the plunger illustrating the parallel ribs and three sections.
Figure 4B:
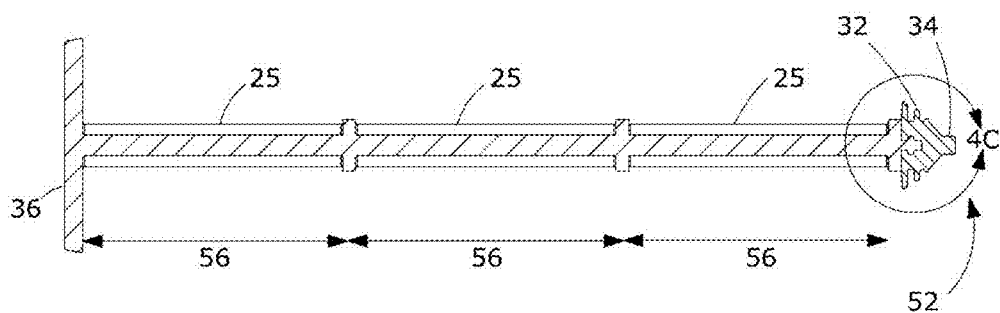
FIG. 4B is a cross-sectional view of the plunger taken along the length of FIG. 4A.
Figure 4C:
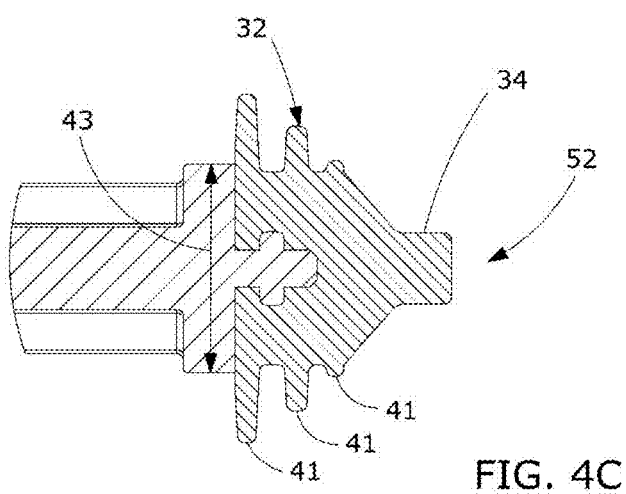
FIG. 4C is an exploded view of the distal end of the plunger rubber rings and extension that is funnel-like shaped to fit into and plug the distal end of the barrel (e.g. one-way valve).
Figure 4D:
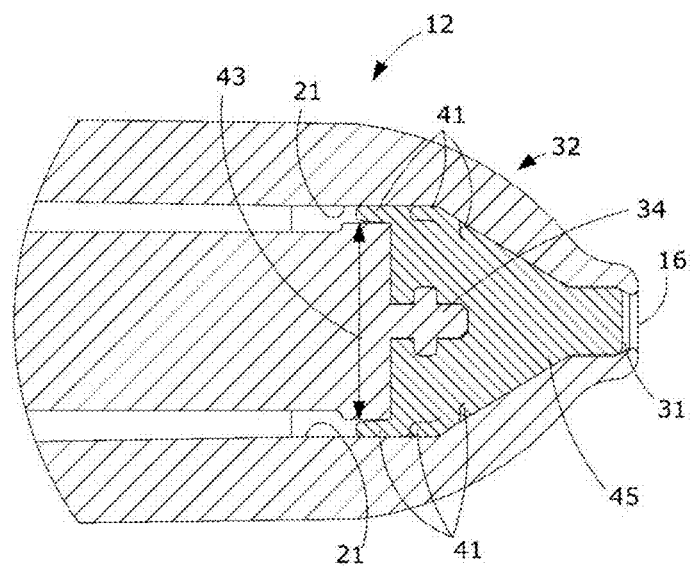
FIG. 4D is an exploded cross-sectional view of the plunger distal end of FIG. 4C.
Figure 5:
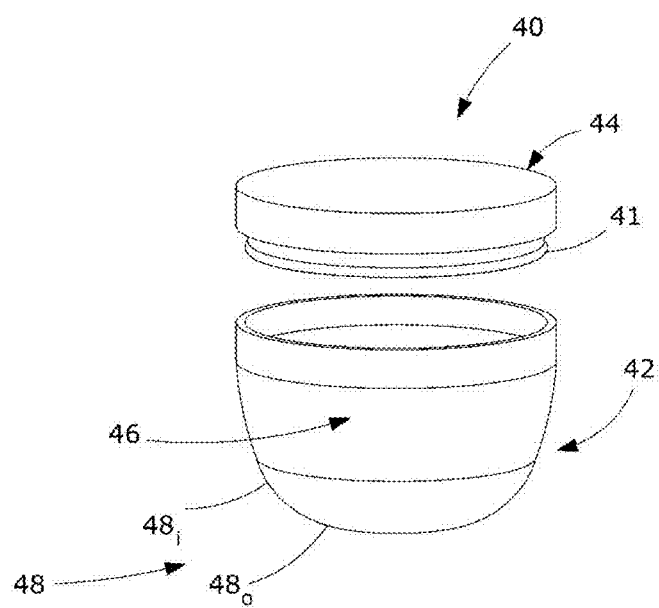
FIG. 5 is a view of an exemplary semen collection jar used within the fertility kits of the present invention.

FIGS. 1-6 illustrate one exemplary embodiment of the fertility kits of the present invention: FIGS. 1-4C, syringe 10; FIG. 5 a semen collection jar 40; and FIG. 6 a fertility kit 50.

Syringe

As illustrated in FIGS. 1-4C, each fertility syringe comprises a proximal end 35 and a distal end 30, and the general components of: an outer barrel 12 with a hollow tube 20 centered along the barrel length; and a plunger 22 that easily slides back and forth through tube 20.

The syringe also has a handle unit combining: circular members 26 attached to the barrel 12; and with a flat head end 36 attached to the plunger 22. This combination allows a user (if necessary), to hold and control the movement of the plunger using just three fingers: thumb, index, and middle finger. Preferably the user has both hands available to stabilize the syringe.

In an exemplary embodiment, syringe 10 is about 125-130 mm in length and about 72 mm in width due to the handle loops 26 (but about 20 mm at barrel 12); and the syringe is made of disposable plastic that is able to be sterilized via exposure to gamma radiation or ethylene oxide.

Syringe Barrel

FIG. 3A is an illustration of an exemplary side view of the outer surface of barrel 12; and FIG. 3B is a longitudinal cross-section view of FIG. 3A, rotated ninety degrees. In an exemplary embodiment, the syringe's barrel comprises: an outer rigid tubular barrel 12, a center hollow tube 20, and a curved distal end 14 (e.g. generally half oval shaped and about 26 mm in length). This distal end further comprises a small circular distal opening 16 (e.g. about 2.4 to 3 mm in diameter).

As shown in the cross-sectional view of FIG. 3B, barrel 12 may be made of solid opaque material 13 (except for the hollow tunnel 20). In another embodiment, the space between barrel outer body 12 and tube 20 is hollow.

The middle of the barrel houses a hollow tube 20 with inner walls 21, and having a cross-sectional area of about 10 mm in diameter, while the entire barrel has a cross-sectional area of about 20 mm, in one exemplary embodiment.

Tube 20 distal end tapers inward to form a funnel-like shape that matches the distal end 52 of the plunger 32, 34 (see FIGS. 4A-4D). This funnel member either: 1) forms a small narrowed distal opening 31, which aligns and may be joined to the barrel distal opening 16; or 2) joins directly to distal opening 16. Either (1) or (2) allows semen to be pulled into and ejected from the hollow tube 20 while the plunger ends 32, 34 can plug barrel hole 16 to function as a one-way valve after the semen is ejected.

The barrel proximal end comprises a perpendicularly positioned disc 18 with a hole 15 equal to the plunger diameter, and forming a sealed proximal end that prevents plunger 22 from fully detaching from barrel 12. Proximal end 18 further comprises one part of the handle combination, two opposing loop members 26.

Plunger

FIG. 4A illustrates a side view of plunger 22; FIG. 4B is a longitudinal cross-sectional view thereof; and FIG. 4C is a magnified view of the plunger's distal end. Plunger 22 slides smoothly distally and proximally through the barrel hollow tube 20, while contacting the tube's inner walls 21 to push all the semen out of the distal opening 16. In an embodiment, the length of plunger 22 is about 135 to 137 mm, the diameter is about 9.5 mm, and the diameter of tube 20 is about 10 mm.

As illustrated in the close-up view of FIG. 4C and cross-sectional view 4D, plunger 22 further comprises on the distal end a circular rubber end 32 (e.g., a plug), with or without individual rings 41 (e.g., 3 total) that are wider than the plunger's diameter 43, and taper downward/inward distally; and may further comprise a tubular extension 34 (e.g., a pin or "pointed tip") adjoined distally to the rubber ring(s) 32. Plunger distal end (52) comprising the rubber end 32 and pin 34 are within a funnel-like shape distal end 45, and are sized to fit tightly into the both the barrel's hollow tube 20 funnel-like shape distal end 31 and the barrel's distal end opening 16 (e.g., see FIG. 3B). This enables the expulsion all of the semen from the syringe, while also functioning as a one-way valve (e.g., the opening 16 is too small and blocked by 32, 34 so as to prevent any semen from re-entering the syringe). In an embodiment, plunger 22 further comprises a plurality of parallel ribs 23 (e.g., 5 total) evenly spaced around the plunger, and extending its length (proximal to distal). Plunger 22 may also be divided into multiple sections 25 along its length, e.g., three sections of about equal length, with a flat disc 17 joining two aligned sections 25. Parallel ribs 23 and sections 25 facilitate plunger 22 to slide smoothly back and forth through tube 20 by minimizing the surface contact area, and by making the plunger more rigid.

Syringe Handles

As illustrated in FIGS. 1-3B, the syringe handle combination comprises: 1) the barrel's two looped rings 26; and 2) the plunger's flat end 36, which is rotated 90 degrees to fit in-between loops 26. Barrel loops comprise two opposing substantially hollow, circular members 26 able fit a user's index and middle fingers. In an embodiment, the inner diameter of circular members 26 is about 25 mm; and the circular members 26 do not form a complete circular, but rather about 75% with an opening (e.g., near the outer rigid tubular barrel 12—see FIGS. 2, 3A, opening 54). In another embodiment, they form a complete hollow circle.

Figure 1:
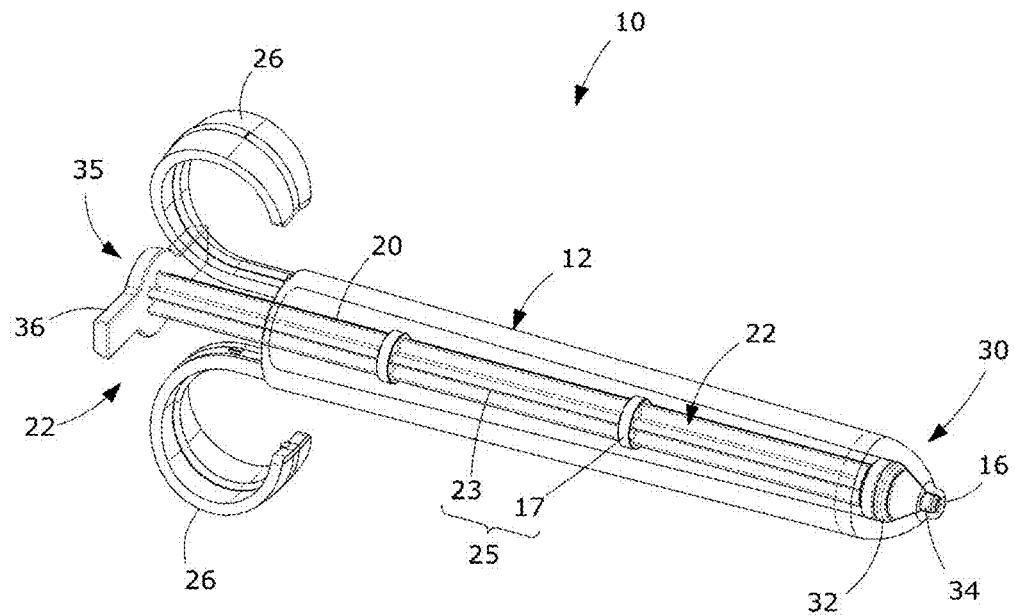
FIG. 1 is a perspective view of the fertility syringe in a closed position with the plunger fully inserted within the barrel.
Figure 2:
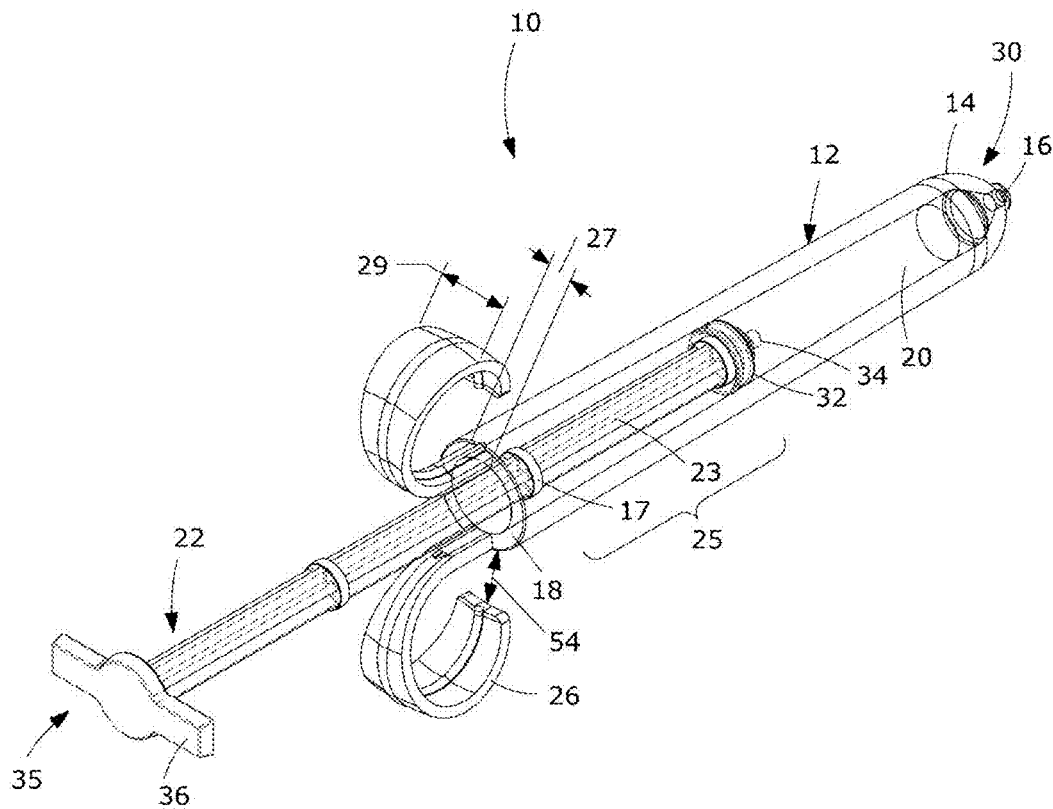
FIG. 2 is another perspective view of the fertility syringe with the plunger partially withdrawn from the barrel.

In an embodiment, the shape of circular members 26 also tapers wider while extending outward from barrel proximal end 18. As shown in FIG. 2, at end 18 the minimum width 27 of a circular member 26 is about 2-3 mm; and the maximum width 29 is about 15 to 16 mm. In another embodiment, circular members 26 have a uniform width the entire length. In all embodiments, plunger flat end 36 is rotated to fit in-between circular members 26 when the plunger is completely pushed in via a user's thumb on flat end 36. Plunger flat end 36 may also comprise a variety of substantially thin about 2 mm flat shapes, such as rectangular, or oval, or the exemplified, center circle with opposing rectangular ends.

Collection Jars

FIG. 5 is an illustration of an exemplary semen collection jar 40 comprising a round hand-held container 42 and a sealable snap-on lid 44 with inner rim 41, Container 42 has an inner surface 46 comprising smooth seamless edges 48 on the outer surface 48o and on the inner surface 48i to prevent semen from being trapped within the seamless edges. In one embodiment, jar 40 can hold up to 30 milliliters volume, and it about 50 mm width on the lid, and about 40 mm height. In an embodiment, the collection jar is made of disposable plastic that is able to be sterilized via exposure to gamma radiation or ethylene oxide.

ICI Fertility Kits

In an exemplary embodiment, kits 50 of the present invention comprise: at least one set (e.g., three sets total) of sterile fertility syringes 10 and sterile collection jars 40, which are shipped in one container (e.g., a substantially rectangular shaped, recyclable, cardboard box 50). For example, one kit comprises one treatment with one collection jar 40 and one packaged syringe 10. A user would buy three kits for one month of treatment. In another embodiment, three sets of collection jars and syringes come in the same package.

Each fertility syringe is individually packaged with a transparent or opaque plastic wrapper 60 to keep the syringe sterile. In another embodiment, two or three fertility syringes are sealed within one plastic wrapper 60. Likewise, each jar is individually packaged with a transparent or opaque plastic wrapper 61 to keep the jar sterile. In another embodiment, two or three jars are sealed within one plastic wrapper 61. In another embodiment, one syringe and one jar are within each plastic wrapper. Wrappers 60, 61 of the present invention are also known in the medical device industry as C-packs, and are made in compliance with ISO 11607-1:2019—"Packaging for terminally sterilized medical devices—Part 1: Requirements for materials, sterile barrier systems and packaging systems". In an embodiment, that C-pack is made of Tyvek™ with pores that allow air, ethylene oxide, and gamma radiation to pass through, but not pathogens (e.g. bacteria, fungi, viruses, etc.). The kits may further comprise printed instructions 62 and/or posted instructions on a website link or QR code 64 to a website that is printed on the outside or inside of the shipping box. Instructions may further comprise a printed calendar, a website link, or a QR code for downloading a calendar of the present invention for a user to track their ovulation cycle.

Ovulation Calendars and Luteinizing Hormone Strips

The ovulation calendar (FIG. 7A, 70) and luteinizing hormone test strips (FIG. 7B, 80) (also known herein as "ovulation test strips") are used to determine the optimal time for the user to attempt insemination, which occurs when the user is ovulating. In embodiment, the ovulation calendar and test strips are in the same kit as the syringes and jars; and in another embodiment, they are mailed separately.

Figure 7A:
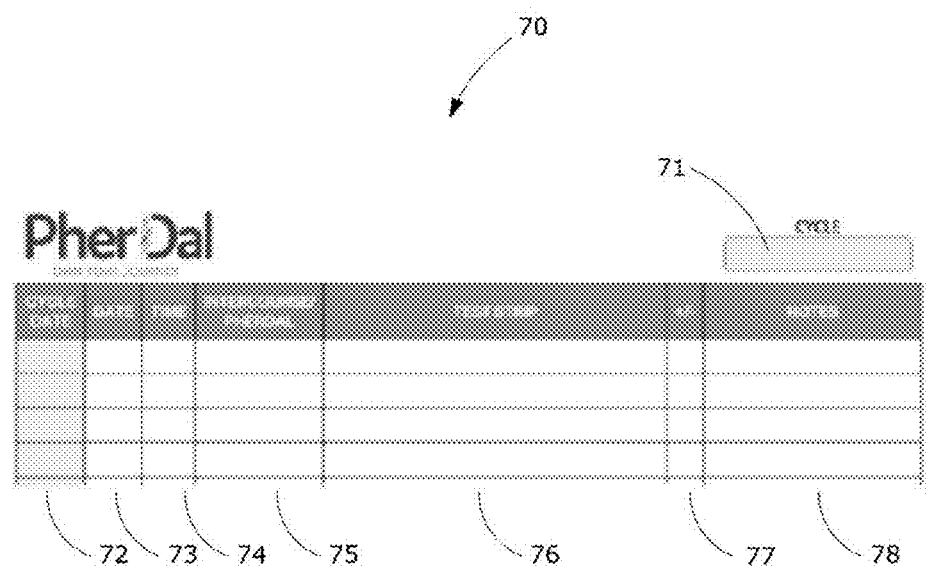
FIG. 7A is an exemplary ovulation calendar of the present invention.
Figure 7B:
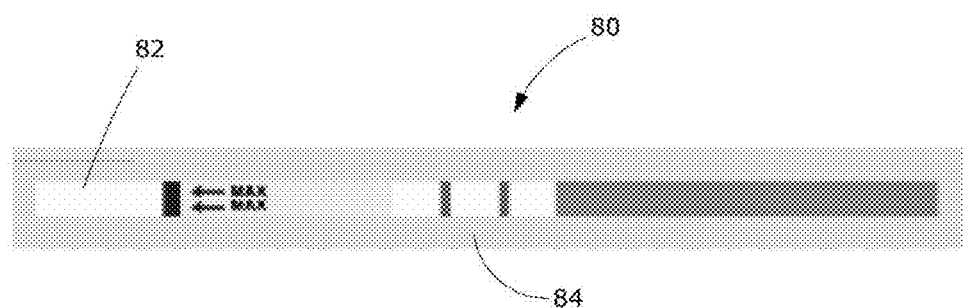
FIG. 7B is an exemplary luteinizing strip of the present invention.

An exemplary luteinizing hormone (LH) test strip 80 is illustrated in FIG. 7B and comprises: a thin rectangular paper that is dipped on end 82 into a cup of the user's fresh urine at a level not to exceed the maximum line. After waiting about 5 minutes, at least one line 84 appears in the middle of the strip 80. If only one line appears, this is the "control" and the results are negative for LH. If two distinct separate lines appear, as illustrated in FIG. 7B, then the first line from end 82 is LH, and the second line from end 82 is the control line, and thus the results are positive for LH.

In an embodiment, the ovulation calendar is a paper table, or an online table able to receive and save user input (e.g. text and images); and comprising columns, e.g.: cycle date 72; date of recording 73; time of recording 74; intercourse 75; LH test strip image 76; "+/−" 77; and Notes 78.

Cycle date 72 refers to menstrual cycle day, wherein "CD1" is the first day of onset. Intercourse 75 refers to whether the user had intercourse on the day of recording 73. LH 76 refers to the luteinizing hormone (LH) test strip identification number or a photo of the strip test results; and "+/−" 77 refers to whether the LH test strip results were positive or negative for the presence of LH. The user can also add notes 78, such as how they are feeling—extreme fatigue, cramps, etc. Once the user begins to see their LH levels rise, they should test 3 times a day to determine when they reach their peak LH level, as indicated when the LH starts to drop again. They should then use kit 60 is inseminate three days in a row: when the think they are about to reach their peak LH level; the day of the peak; and the day after. The ovarian egg is released about 24 hours after the peak LH level, and it can only be fertilized by the semen deposited using the syringe for the next 24 hours. So, there is only about a 48 hour window to optimize the user's chance of a pregnancy occurring.

Method of Use of Kits

The method of use of kits 50 comprise the user first determining their ovulation cycle. This can be done using a calendar downloaded herein, and/or by using a third-party test kit or strips for measuring their luteinizing hormone level (e.g., a non-digital ovulation predictor kit—OPK). A user first determines when they are near their monthly maximum luteinizing hormone level by using the ovulation calendar (FIG. 7A, 70) and luteinizing hormone test strips (FIG. 7B, 80). In an embodiment, the ovulation calendar and test strips are in the same kit as the sets of syringes and jar; and in another embodiment, they are mailed separately.

Then semen donor deposits a fresh semen sample, or the user can use a recently thawed semen sample, that is deposited into a clean, sterile semen collection jar 40 and sealed closed.

The user then removes the lid 44, unwraps a sterile syringe 10, and positions the syringe vertically in collection jar 40. The user then pulls up on plunger 22 until all of the semen is within the syringe. In an additional embodiment, the user may re-use the syringe while still lying down, so as to inject all of the semen remaining in the jar (e.g., two or more consecutive injections). The syringe distal end is not laid down or touched in between injections.

Then while lying down and holding the syringe in their dominant hand using their index and middle fingers inserted into syringe loops 26, the user inserts the distal end of the syringe into their vagina until it is flush with their cervical opening. They then push the plunger handle 36 inward or distally with their thumb to release all of the semen sample into their cervical opening (e.g., plunger distal ends 32, 34 are against barrel hole 16 and the plunger cannot further move distally). After administering the semen sample or specimen, the user should remain lying down for at least a half hour.

In an embodiment, each kit 50 comprises three sets of syringes 10 and collection jars 40; for use the day before, of, and after ovulation, as indicated by a user's maximum luteinizing hormone strips to test. Hence, the user should administer a semen sample during these three days (i.e. day before peak, day of peak, day after peak). If a pregnancy does not result, the user can repeat the process in a subsequent month. As with all forms of infertility treatment, it could take 3-6 months in order for the user to become pregnant with this method of ICI.

Method of Kit Sterilization

Figure 8:
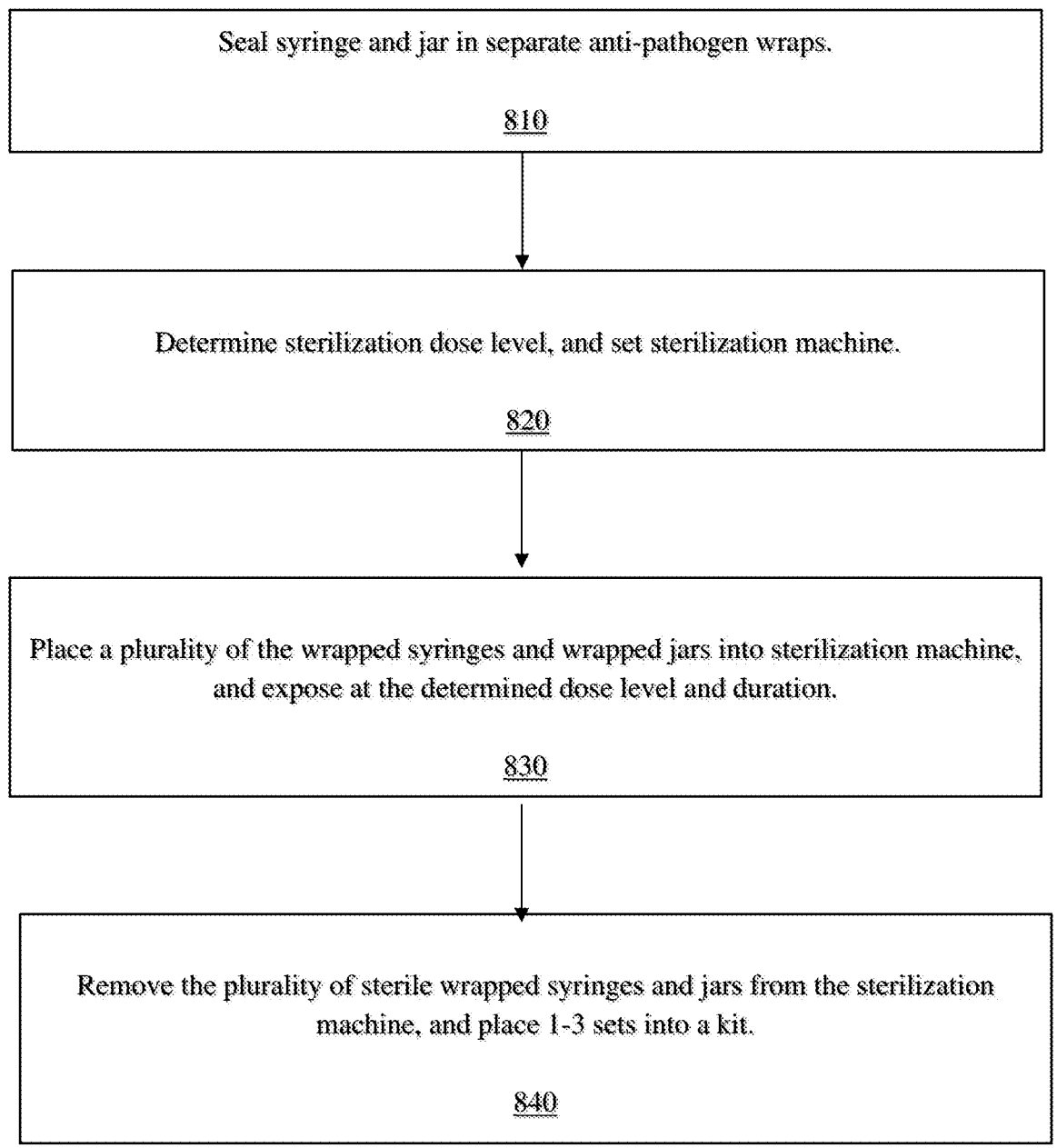
FIG. 8 is a flowchart of steps in performing sterilization of the kit components.

FIG. 8 is a flowchart of user steps in terminally sterilizing the syringes and jars of the present invention. They are "terminally sterilized" in accordance with the International Organization of Standardization (ISO) regulation ISO 11607, which is hereby incorporated by reference in the entirety. The syringes and jars of the present invention are "terminally sterilized" by undergoing a sterilization process while the product is already within its packaging (C-pack; wrapper 60, 61), which includes a sterile barrier system. A sterile barrier system is the minimum layer of protection that ensures sterility.

The "packaging system" as a whole is a combination of the sterile barrier system and any protective packaging (e.g. kit box) used to prevent damage to the sterile barrier system or the device. Terminally sterilized devices are sterilized using an agent that can penetrate their packaging system, such as ethylene oxide or gamma radiation. In an embodiment, the sterile barrier system comprises Tyvek™ material (a polypropylene blend) completely enclosing and sealing off at all seams the syringe and jar, in the same or different wraps (FIG. 8, step 810). Other materials well known in the art for use in the C-packs are also envisioned within the scope of the present invention, wherein the type and density of material largely determines that dose level and duration of sterilization ("Gamma Sterilization of Medical Devices", FDA MEDICAL DEVICE ADVISORY MEETING Nov. 6, 2019, table "Plastics Comparison"). For example, polyesters can sustain up to 10,000 kilogray (kGy), while polypropylene only requires up to 50 kGy.

Methods of sterilizing medical devices using ethylene oxide or gamma radiation are well known in the art. In the sterilization of medical devices via exposure to ethylene oxide, the exposure conditions used are those required as listed in ANSI AAMI ISO 11135:2014, and ANSI AAMI ISO 10993-7:2008(R)2012. Ethylene oxide sterilization requires three phases: preconditioning; chamber cycle; and aeration (e.g. see Reisbacher, S, "Introduction to Ethylene Oxide Sterilization and Regulatory Updates", 22 May 2019, pages 1-54). For example, preconditioning is performed at about 35-45 degrees Celsius and about 45-75% relative humidity; the chamber cycle is performed in cycles up to about 850 mbarA; the aeration is performed at about 35-50 degrees Celsius with forced circulation. In another embodiment, the temperature is between about 37 to 63 degrees Celsius, or about 104-140 degrees Fahrenheit; at a fixed pressure; concentration of about 500-800 mg/L and inversely dependent on the temperature; and exposed for about 2-10 hours, and aerated for about 7-10 days.

The gamma sterilization process is significantly different than the ethylene oxide process, and it starts by placing the source of radiation (usually Cobalt 60, but sometimes Caesium 137) in a radiation-shielded room. Packaged medical devices are then brought in using a conveyance system and circulated around the source of radiation to expose all sides of the product to the gamma rays.

In contrast to sterilization methods like ethylene oxide (EO), gamma irradiation does not require strict humidity, temperature, or pressure controls. The gamma sterilization process also does not significantly increase the temperature of the products being treated, making it ideal for sterilizing heat sensitive devices.

Radiation sterilization is performed under ISO 11137-1, which covers gamma, x-ray, and e-beam. In an embodiment, gamma radiation is performed on a plurality of syringes and jars at ambient temperature up to 20 degrees Celsius; for up to 24 hours; at a dose level of about 20-50 kilogray (kGy) (FIG. 8, step 820); and no requirement for fixed pressure.

Sterilization dose determination is performed by methods outlined in ISO 11137-1 and 2. The minimum dose [or sterilization dose (Dster) [as defined in ISO 11137] is the minimum dose defined to achieve the desired sterility assurance level, typically SAL $10^{-6}$. The minimum dose is established to be in accordance with ISO 11137-2.

A maximum dose must also be established and not exceeded during gamma sterilization because gamma rays have the potential to break down the polymers that are used in many single-use medical devices that require sterilization. ISO 11137-2 offers three related methods for establishing a radiation dose that meets both these requirements. The first two methods are similar to each other and involve determining the natural bioburden—the number of microorganisms on a product—and verifying the appropriate dose via sterility testing. These methods are designed to be used with products that come in large batches and require at least 100 units of the product. The third method, known as VDmax, is used for products that are made in smaller batches, when grouping hundreds of devices together is not feasible. Instead of determining the minimum dose required to reach SAL $10^{-6}$, this method tests a predetermined dose: either 25 kGy or 15 kGy for products with a lower tolerance for gamma rays.

In an embodiment, dose mapping may be required, and is performed in accordance with ISO 11137 rules and the International Atomic Energy Agency (IAEI) rules—e.g. see "Guidelines for the Development, Validation, and Routine Control of Industrial Radiation Processes", the entirety of which is incorporated herein by reference.

Figure 6:
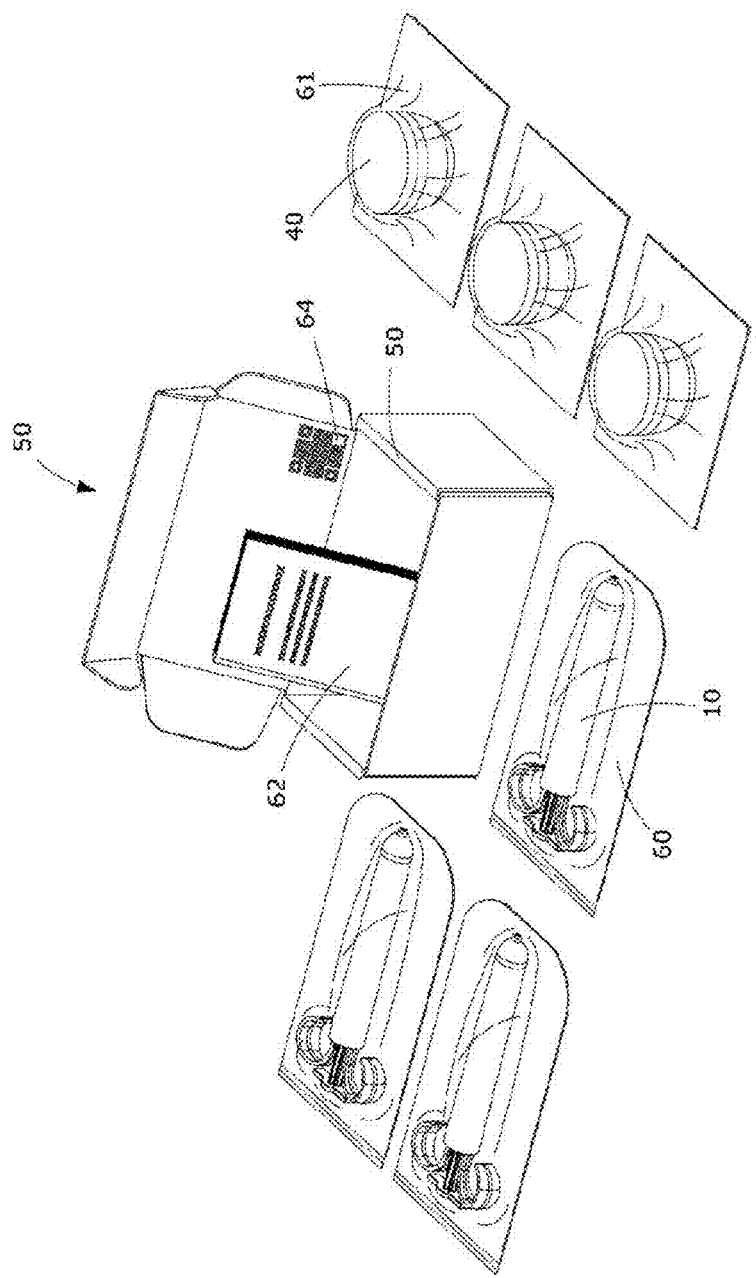
FIG. 6 is an illustration of a kit comprising plastic wrappers sealing the syringes and collection jars to keep them sterile, and wherein the round collection jars do not have inner seams where semen residue could be trapped.

In an embodiment, up to about 500 wrapped syringes and 500 wrapped jars of the present invention that are C-packaged, are placed into large cardboard boxes and placed on a pallet, and then placed into a gamma radiation device (e.g. Steris™ Corporation, Cobalt-60 gamma radiation device, at about 25 kGy, and at room temperature) (FIG. 8, step 830). The pallet is rotated around the gamma beam for up to 24 hours, then one to three sets of the sterilized, wrapped syringes and the sterilized, wrapped jars are placed in each kit (FIG. 8, step 840) as shown in FIG. 6.

As shown in FIGS. 7A and 7B, an ovulation calendar 70 and/or luteinizing hormone strips 80 are added to the kit, or preferably shipped separately.

CONCLUSION

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

All cited publications are incorporated herein in their entirety. Trademarks are the property of their registered owners.

What is claimed is:

1. A sterile intracervical insemination (ICI) fertility kit for performing at home self-insemination, comprising at least one set of:
   a) a wrapped, sterilized disposable plastic fertility syringe (10) comprising,
      i) an outer rigid tubular barrel (12), comprising a curved distal end (14) with a distal opening (16) and a sealed proximal end (18), and said barrel enclosing an inner hollow tube (20) with a narrowed distal end at an opening (31) joined to the barrel distal opening (16);
      ii) the barrel sealed proximal end (18) further comprising a handle combination comprising two opposing substantially hollow circular members (26) forming about 75% or 100% of a complete circle, and a centered proximal flat handle (36);
      iii) a plunger (22) positioned within the inner hollow tube (20) and able to slide within said tube (20) to draw up and expel semen from the barrel distal opening (16), with a plunger distal end (52) encircled by a rubber seal (32) comprising a plurality of flexible rings (41) decreasing in diameter distally and able to prevent semen backflow;

b) a wrapped, sterilized, disposable plastic semen collection jar (40) comprising:
  i) a hand-held container (42), with round shaped smooth seamless edges (48) on an inner surface (48i) and outer surface (48o) on the hand-held container, the seamless edges of the inner surface (48i) able to prevent the semen from being trapped within the seamless edges;
  ii) a sealable lid (44), comprising a snap-on lid or screw threads; and
c) a flat sealed plastic wrap enclosing each of the syringe and the collection jar together in a same wrap or in a separate wrap, wherein the wrap is permeable to air and gas, and impermeable to pathogens, and the wrapped syringe and jar are sterilizable via exposure to ethylene oxide or gamma radiation.

2. The OTC fertility kit of claim 1, wherein the plurality of flexible rings (41) are wider than a plunger diameter (43) to prevent semen backflow proximally.

3. The ICI fertility kit of claim 2, wherein the plunger further comprises a pin (34) distal to the rubber seal (32), said pin positioned to fit tightly within the tube narrowed distal opening (31) to plug the syringe from semen backflow.

4. The ICI fertility kit of claim 1, wherein the plunger distal end (52) is shaped to fit snugly into the inner hollow tube (20) distal end to push all of the semen out of the barrel distal opening (16), while preventing semen backflow.

5. The ICI fertility kit of claim 1, wherein the plunger (22) further comprises parallel ribs (23), divided into three sections (25) of about equal length, the parallel ribs encircling and extending a length of the plunger to stiffen the plunger.

6. The ICI fertility kit of claim 1, wherein the collection jar holds about a 30-34 milliliter volume; and the sealable lid is the snap-on lid.

7. The ICI fertility kit of claim 1, wherein the semen is washed or unwashed, and fresh or frozen.

8. The ICI fertility kit of claim 1, further comprising a container (50) for shipping the one or more sets, said container comprising printed instructions on a method of using the fertility kit, or a printed website link, or a QR code to said instructions.

9. The ICI fertility kit of claim 1, further comprising an ovulation calendar (70) to track luteinizing hormone result levels; and a plurality of luteinizing hormone test strips (80).

10. The ICI fertility kit of claim 1, wherein both the plunger distal end (52) and the inner tube (20) distal end are funnel-like shaped to snugly fit together to push all of the semen out of the barrel distal opening (16), while preventing semen backflow.

11. The ICI fertility kit of claim 1, further comprising an ovulation calendar (70) to track luteinizing hormone result levels; or a plurality of luteinizing hormone test strips (80).

12. A method of sterilizing an intracervical insemination (ICI) fertility kit, comprising:
 1) sealing an ICI fertility syringe and a semen collection jar in a plastic wrap, wherein the syringe and the jar are in a same wrap or a separate wrap, and the plastic wrap is permeable to air and gas, and impenetrable to pathogens, wherein the ICI fertility syringe and the semen collection jar comprise:
  a) a wrapped, sterilized disposable plastic fertility syringe (10) comprising,
   i) an outer rigid tubular barrel (12), comprising a curved distal end (14) with a distal opening (16) and a sealed proximal end (18), and said barrel enclosing an inner hollow tube (20) with a narrowed distal end at an opening (31) joined to the barrel distal opening (16);
   ii) the barrel sealed proximal end (18) further comprising a handle combination comprising two opposing substantially hollow circular members (26) forming about 75% or 100% of a complete circle, and a centered proximal flat handle (36);
   iii) a plunger (22) positioned within the inner hollow tube (20) and able to slide within said tube (20) to draw up and expel semen from the barrel distal opening (16), with a plunger distal end (52) encircled by a rubber seal (32) comprising a plurality of flexible rings (41) decreasing in diameter distally and able to prevent semen backflow;
  b) a wrapped, sterilized, disposable plastic semen collection jar (40) comprising:
   i) a hand-held container (42), with round shaped smooth seamless edges (48) on an inner surface (48i) and outer surface (48o) on the hand-held container, the seamless edges of the inner surface (48i) able to prevent the semen from being trapped within the seamless edges;
   ii) a sealable lid (44), comprising a snap-on lid or screw threads; and
  c) wherein each wrapped syringe and jar are is sterilizable via exposure to ethylene oxide or gamma radiation;
 2) determining a sterilization dose level and duration, and setting a sterilization machine to the dose level, wherein the sterilization machine emits ethylene oxide or gamma radiation;
 3) placing a plurality of the wrapped syringes and the wrapped jars into the sterilization machine, and exposing to sterilization at the determined dose level and duration; and
 4) removing the plurality of sterile wrapped syringes and wrapped jars from the sterilization machine, and placing one to three sets of the syringes and jars into a kit.

13. The method of claim 12, wherein the sterilization machine emits gamma radiation at a dose level about 20-50 kilograys, and for a duration up to 24 hours.

14. The method of claim 12, wherein the gamma radiation is emitted from Cobalt.

15. The method of claim 12, wherein the sterilization machine emits ethylene oxide up to 7 days duration.

16. The method of claim 12, wherein the plurality of flexible rings (41) are wider than a plunger diameter (43) to prevent semen backflow proximally.

17. The method of claim 12, wherein the plunger further comprises a pin (34) distal to the rubber seal (32), said pin positioned to fit tightly within the tube narrowed distal opening (31) to plug the syringe from semen backflow.

18. The method of claim 12, wherein the plunger distal end (52) is shaped to fit snugly into the tube (20) distal end to push all of the semen out of the barrel distal opening (16), while preventing semen backflow.

19. The method of claim 12, wherein the plunger (22) further comprises parallel ribs (23), divided into three sections (25) of about equal length, the parallel ribs encircling and extending a length of the plunger to stiffen the plunger.

20. The method of claim 12, wherein the kit further comprises a container (50) for shipping the one or more sets, said container comprising printed instructions on a method of using the fertility kit, or a printed website links, or a QR code to said instructions.

21. The method of claim 12, wherein both the plunger distal end (52) and the inner tube (20) distal end are funnel-like shaped to snugly fit together to push all of the semen out of the barrel distal opening (16), while preventing semen backflow.

22. A method of using an intracervical insemination (ICI) fertility kit for performing at home self-insemination, comprising the steps of:
1) Providing a fertility kit housing at least one sterile wrapped set of ICI syringes and semen collection jars, the at least one sterile wrapped set comprising:
    a) a wrapped, sterilized disposable plastic fertility syringe (10) comprising,
        i) an outer rigid tubular barrel (12), comprising a curved distal end (14) with a distal opening (16) and a sealed proximal end (18), and said barrel enclosing an inner hollow tube (20) with a narrowed distal end at an opening (31) joined to the barrel distal opening (16);
        ii) the barrel sealed proximal end (18) further comprising a handle combination comprising two opposing substantially hollow circular members (26) forming about 75% or 100% of a complete circle, and a centered proximal flat handle (36);
        iii) a plunger (22) positioned within the inner hollow tube (20) and able to slide within said tube (20) to draw up and expel semen from the barrel distal opening (16), with a plunger distal end (52) encircled by a rubber seal (32) comprising a plurality of flexible rings (41) decreasing in diameter distally and able to prevent semen backflow;
    b) a wrapped, sterilized, disposable plastic semen collection jar (40) comprising:
        i) a hand-held container (42), with round shaped smooth seamless edges (48) on an inner surface (48i) and outer surface (48o) on the hand-held container, the seamless edges of the inner surface (48i) able to prevent the semen from being trapped within the seamless edges;
        ii) a sealable lid (44), comprising a snap-on lid or screw threads;
    c) a flat sealed plastic wrap enclosing each of the syringe and the collection jar together in a same wrap or in a separate wrap, wherein the wrap is permeable to air and gas, and impermeable to pathogens, and the wrapped syringe and jar are sterilizable via exposure to ethylene oxide or gamma radiation;
2) determining a user's calendar date of displaying a maximize luteinizing hormone (LH) level;
3) receiving a fresh or frozen deposit of a clean semen sample within a semen collection jar of one of the at least one set;
4) holding an unwrapped, sterile fertility syringe of the one of the at least one set vertically in the sterile collection jar, and withdrawing all of the semen sample into the fertility syringe by pulling upward on the plunger;
5) while lying down, insert the fertility syringe until it is flush with a user's cervix, then push the plunger distally to release all of the semen sample into the cervix;
6) remaining lying down for at least a half hour; and
7) repeat steps (1)-(6) two more times; for three total injections to occur a day before, a day of, and a day after a user's maximum luteinizing hormone level.

23. The method of claim 22, wherein the plurality of flexible rings (41) are wider than a plunger diameter (43) to prevent semen backflow proximally.

24. The method of claim 22, wherein both the plunger distal end (52) and the inner tube (20) distal end are funnel-like shaped to snugly fit together to push all of the semen out of the barrel distal opening (16), while preventing semen backflow.

* * * * *